(12) United States Patent
Ma

(10) Patent No.: US 8,512,768 B2
(45) Date of Patent: Aug. 20, 2013

(54) PAIN RELIEVING COMPOSITION

(71) Applicant: Edna Ma, Los Angeles, CA (US)

(72) Inventor: Edna Ma, Los Angeles, CA (US)

(73) Assignee: Miss Smarty Pants Enterprises, Inc., Los Angeles, CA (US)

( * ) Notice: Subject to any disclaimer, the term of this patent is extended or adjusted under 35 U.S.C. 154(b) by 0 days.

(21) Appl. No.: 13/623,648

(22) Filed: Sep. 20, 2012

(65) Prior Publication Data

US 2013/0017282 A1 Jan. 17, 2013

Related U.S. Application Data

(63) Continuation-in-part of application No. 13/033,599, filed on Feb. 23, 2011, now Pat. No. 8,293,288.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 6,967,023 | B1 | 11/2005 | Eini et al. |
| 7,241,456 | B2 | 7/2007 | Vromen |
| 7,282,224 | B1 | 10/2007 | Roederer |
| 7,682,623 | B2 | 3/2010 | Eini et al. |
| 7,754,240 | B2 | 7/2010 | Staniforth et al. |
| 2003/0138505 | A1 | 7/2003 | Fischer et al. |
| 2004/0122105 | A1 | 6/2004 | Bettle, III et al. |
| 2007/0292461 | A1 | 12/2007 | Tamarkin et al. |
| 2008/0038219 | A1 | 2/2008 | Mosbaugh et al. |
| 2008/0206159 | A1 | 8/2008 | Tamarkin et al. |
| 2008/0299220 | A1 | 12/2008 | Tamarkin et al. |
| 2010/0015184 | A1 | 1/2010 | Tuel |

*Primary Examiner* — Michael Meller
(74) *Attorney, Agent, or Firm* — Lowry Blixseth LLP; Scott M. Lowry

(57) ABSTRACT

A pain relieving composition that includes an anesthetic in the range of 0.5%-7.0% by weight ("w/w"), an anti-inflammatory agent in the range of 1.0%-11.0% w/w, a moisturizing agent in the range of 0.5%-12.0% w/w, a humectant in the range of 0.5%-13.0% w/w, a penetration enhancing agent in the range of 0.5%-7.0%, and a carrier solvent in the range of 40.0%-97.0% w/w to be used before and/or after procedures which cause damage to human skin.

1 Claim, No Drawings

PAIN RELIEVING COMPOSITION

BACKGROUND OF THE INVENTION

The present invention is generally directed to topical pain relieving compositions. More particularly, the present invention relates to topical pain relieving compositions used for the treatment of skin before and/or after the removal of human body hair, waxing (with soft or hard wax), laser hair removal, tattoo application or removal, sugaring, permanent make-up applications and/or any other procedure where the epidermis may be damaged.

Generally, during various body hair removal or laser tattoo removal procedures, an individual will experience pain and damage to the epidermis. Procedures such as waxing and laser tattoo removal are basically a localized control burning of the skin, which results in mild burn-like damage such as redness, mild swelling, irritation, inflammation and dryness. This pain and damage is especially unpleasant upon sensitive areas such as an individual's bikini line. Presently, topical pain relieving compositions used to alleviate pain during processes such as waxing (with soft or hard wax), laser hair removal, shaving, tweezing, electrolysis and tattooing or tattoo removal, sugaring, and permanent make-up applications do not simultaneously treat skin damage.

Accordingly, there is a need for a topical pain relieving composition to be used during processes which damage a person's skin which not only minimizes the pain, but soothes, heals, decreases inflammation and moisturizes the skin as well. Such a composition should include ingredients such as an anesthetic to reduce pain, an anti-inflammatory to sooth and heal, a moisturizing agent, a humectant, a penetration enhancing agent, a thickener, an emollient, a solvent stabilizer, a preservative, an emulsifier, an ultraviolet absorber, a colorant, and a carrier solvent. The present invention fulfills these needs and provides further related advantages.

SUMMARY OF THE INVENTION

The pain reliving composition disclosed herein preferably includes an anesthetic in the range of 0.5%-7.0% by weight ("w/w") of the composition, an anti-inflammatory agent in the range of 1.0%-11.0% w/w of the composition, a moisturizing agent in the range of 0.5%-12.0% w/w of the composition, a humectant in the range of 0.5%-13.0% w/w of the composition, a penetration enhancing agent in the range of 0.5%-7.0% w/w of the composition, and a carrier solvent in the range of 50.0%-97.0% w/w of the composition.

The anesthetic may be any combination of local anesthetics, including benzocaine, capsaicin, lidocaine, prilocaine, tetracaine or pramoxine. Preferably, the composition includes lidocaine, capsaicin or pramoxine in the range of 2.5%-6.0% w/w to ensure adequate numbing of the epidermis and dermis. Even more preferably, the composition includes 4% w/w of lidocaine.

The anti-inflammatory agent of the composition may include a natural agent or a non-steroidal anti-inflammatory drug (hereinafter "NSAID"). Natural agents may include Aloe barbadensis leaf juice, Ginger root extract, chamomile oil, grape seed extract, marigold extract, tea tree oil, lavender oil, peppermint oil or mint oil. NSAIDs may include acetyl salicylic acid, diclofenac, ibuprofen, ketoprofen or piroxicam. Preferably, the composition includes 1.5%-6.0% w/w of Aloe barbadensis leaf juice, tea tree oil, peppermint oil or diclofenac to reduce inflammation which further soothes the damaged area of skin and promotes healing. Even more preferably, the composition includes 2.5% w/w of aloe barbadensis leaf juice which adequately soothes and heals damaged skin.

The moisturizing agent may include jojoba (simmondsia chinensis) seed oil, palm oil, coconut oil, almond oil, olive oil or castor oil. Preferably, the composition includes 0.5%-10.0% w/w of jojoba seed oil, and even more preferably, 1.0% w/w of jojoba seed oil, which enables the composition to provide the skin with all day moisturization.

The humectant may include hexylene glycol, propylene glycol, butylene glycol, sorbitol or glycerin. Preferably, the composition includes 0.5%-10.0% w/w of hexylene glycol or propylene glycol which attracts water and prevents the loss of moisture from the skin. Even more preferably, the composition includes 1.0% w/w of hexylene glycol.

The penetration enhancing agent may include dimethyl sulfoxide (DMSO), ethanol, disodium ethylenediaminetetraacetic (EDTA) or lauramide DEA. Preferably, the composition includes 0.5%-5.0% w/w of DMSO in order to ensure adequate penetration of the anesthetic through the cutis. The composition may also preferably include 2.5% w/w of DMSO to ensure adequate skin absorption by the anesthetic.

The carrier solvent may include water or mineral oil. Preferably, the carrier solvent includes 52.0%-94.0% w/w of water to add moisture to the skin and provide the composition with a non-greasy feel.

Additionally, the composition may include a thickener in the range of 2.0%-10.0% w/w of the composition. The thickener may include cetyl alcohol, xanthan gum, beheny alcohol, carbomer or hydroxypropyl methycellulose. Preferably, the composition includes 3.0%-8.0% w/w of cetyl alcohol to provide the composition with higher viscosity. Even more preferably, the composition includes 6.5% w/w of cetyl alcohol giving the composition its desired viscosity, texture and spreadability.

The composition may further include sodium polyacrylate and caprylyl glycol. Preferably, the composition includes 0.5%-5.0% w/w of sodium polyacrylate, which provides skin conditioning properties because of its ability to hold 400-500 times its weight in water, and 0.05%-4.0% w/w of caprylyl glycol to further stabilize the composition. Even more preferably, the composition includes 1.5% w/w of sodium polyacrylate and 0.3% w/w of caprylyl glycol.

In addition to ingredients above, the composition may also include an emulsifier in the range of 0.5%-5.0% w/w. Preferably, the emulsifier may include stearic acid or glyceryl monostearate. Even more preferably, the composition includes 2.5% w/w of stearic acid which provides proper emulsification.

The composition may also include a preservative of potassium sorbate, phenoxyethanol, methylparaben or polyparaben. Preferably, the preservative includes potassium sorbate in the range of 0.0005%-1.0% w/w of the composition and phenoxyethanol in the range of 0.0005%-1.0% w/w. Even more preferable, the composition includes 0.001% potassium sorbate and 0.5% w/w phenoxyethanol which would adequately inhibit microorganism development and enhance the composition's shelf-life.

Furthermore, the composition may also include an ultraviolet absorber in the range of 0.05%-2.0% w/w of the composition and a colorant in the range of 0.05%-2.0% w/w. The ultraviolet absorber may include benzophenone-4 or benzophenone-3 and the colorant may include any color of dye which would not color the skin when applied. The colorant selected should also be distinct from any color emulating bodily exudates. Preferably, the colorant includes blue 1, blue 2, blue 10 or blue 40, the ultraviolet absorber includes 0.15% of benzophenone-4 to add sunscreen properties to the composition, and the colorant includes 0.08% of blue 1 giving the composition its distinct color.

Accordingly, the topical pain relieving composition described herein could include any combination of the above described embodiments. All of the above-identified ingredients could be mixed and matched depending on the desired effect of the pain relieving composition. Preferably, the combination of the above-identified ingredients produces a pain relieving composition that soothes, moisturizes, heals and protects the skin.

Other features and advantages of the present invention will become apparent from the following detailed description, when taken in conjunction with the accompanying drawings, which illustrate, by way of example, the principles of the invention.

DETAILED DESCRIPTION OF THE PREFERRED EMBODIMENTS

The human skin is composed of two layers: (1) the outer layer called the epidermis; and (2) the layer directly underneath called the dermis. Together, the layers form what is called the cutis. The epidermis is composed of 5 sublayers: the stratum corneum, the stratum lucidum, the stratum spinosum and the stratum germinativum. Its main function is to protect the body from injury and the outside environment.

The dermis, on the other hand, is the layer beneath the epidermis that includes connective tissue which cushions the body from stress and strain. It is structurally divided into two areas: a superficial area adjacent to the epidermis, called the papillary region, and a deeper and thicker area known as the reticular region. Within the dermis lie the Mechanoreceptors (nerve endings) which provide the individual with their sense of touch, as well as their sensitivity to pain and heat. The dermis also contains the hair follicles, sweat glands, sebaceous glands, apocrine glands, lymphatic vessels and blood vessels. For hair removal, the composition preferably penetrates to the dermis to maximize numbing effectiveness.

During hair removing procedures such as waxing (with soft or hard wax) and laser removal, the various layers of the epidermis and dermis are damaged. These layers of the skin are essentially torn or ripped off, or in the instances of waxing and laser tattoo removal, are mildly burned, causing the individual significant pain. Afterwards individuals experience redness, irritation, inflammation, swelling and dryness to the treated areas. The pain relieving composition disclosed herein is used, not only for the purpose of numbing a localized area of the skin before any painful procedure, but may also be used afterwards to relieve pain. The pain relieving cream should also heal, soothe and moisturize the skin of any redness, irritation, swelling, inflammation or dryness that may occur. The pain relieving composition may be used before and/or after any of the following procedures: body hair removal with wax, shaving, tweezing, laser hair removal, tattooing or tattoo removal, sugaring, permanent make-up applications, electrolysis as well as a pain reliever for sunburns.

Additionally, the cream may be used as a desensitizing agent to improve sexual performance of males suffering from premature ejaculation. Prior to sexual intercourse, a male individual may apply the cream to his penis in order to reduce sensitivity which would allow him to prolong the act of sexual intercourse, thus improving his performance.

Prior to any procedure that may cause damage to the epidermis and/or dermis; the user would apply the subject pain reliving cream to the skin area before treatment in order to preemptively numb the area in anticipation of pain. For hair removal with wax, the pain relieving composition is applied to the skin and left for a period of time sufficient to allow the anesthetic to absorb through the epidermis and into the dermis where the nerve endings and hair follicles reside, numbing the area before treatment. The individual will experience numbing effects as quickly as 10-15 minutes. Preferably, the time sufficient to allow the anesthetic to absorb into the dermis that allows for a maximum numbing effect is approximately 30 minutes. While the pain relieving composition is allowed to take effect, the area may optionally be covered either with a wrapping or piece of clothing. Once the anesthetic has taken effect, any excess lotion is wiped off sufficiently preparing the area of skin for the hair removal procedure. Once the wax is applied and pulled off, removing the hair from the skin, the pain relieving composition may be reapplied to further relieve pain as well as to heal, soothe and moisturize the treated area.

The pain relieving composition preferably includes an anesthetic in the range of 0.5%-7.0% by weight ("w/w") of the composition, an anti-inflammatory agent in the range of 1.0%-11.0% w/w of the composition, a moisturizing agent in the range of 0.5%-12.0% w/w of the composition, a humectant in the range of 0.5%-13.0% w/w of the composition, a penetration enhancing agent in the range of 0.5%-7.0% w/w of the composition, and a carrier solvent in the range of 50.0%-97.0% w/w of the composition.

The anesthetic may include benzocaine, capsaicin, lidocaine, prilocaine, tetracaine or pramoxine. Once absorbed through the epidermis and into the dermis where the nerve endings reside, the listed anesthetics all provide a numbing sensation and pain relieving properties by preventing the transmission of nerve impulses. Preferably, the composition includes lidocaine, capsaicin or pramoxine in the range of 2.5%-6.0% w/w to ensure adequate numbing of the area of skin to be treated. Even more preferably, the composition includes 4% w/w of lidocaine.

The anti-inflammatory may include a natural agent, such as Aloe barbadensis leaf juice, Ginger root extract, chamomile oil, grape seed extract, marigold extract, tea tree oil, lavender oil, peppermint oil, mint oil, salvia officinalis (sage) leaf extract, chamomilla recutita (matricaria) flower extract, tocopherol or allantoin. The above listed natural agents all contain various enzymes, vitamins, and biologically active compounds which provide anti-inflammatory, anti-bacterial, antimicrobial, disinfectant, analgesic (pain-killing) properties that not only soothe the skin after damage, but promote healing as well. When applied before skin damaging procedures, they may soften the skin to ease hair removal. For example, tocopherol contains vitamin E that functions as an antioxidant and balances inflammation associated with the skin. In this respect, tocopherol is suitable for healing the skin (e.g., reducing scarring after a skin injury). Allantoin works as a moisturizer to increase water content and enhance desquamation of the epidermis, it also increases skin smoothness, acts as an anti-irritant, and serves as a skin protectant. When applied afterwards, these ingredients help to heal and soothe damaged skin with their anti-inflammatory and anti-bacterial proprieties. In one embodiment, the composition may include 1.0%-6.0% w/w of Aloe barbadensis leaf juice, tea tree oil or peppermint oil and more preferably includes 1.0%-4.5% w/w of Aloe barbadensis leaf juice. In an alternative embodiment, the composition may include 0.5%-2.5% w/w of salvia officinalis (sage) leaf extract, chamomilla recutita (matricaria) flower extract, tocopherol, or allantoin. In a particularly preferred embodiment, the composition includes therapeutic effective amounts of salvia officinalis (sage) leaf extract, chamomilla recutita (matricaria) flower extract, tocopherol, and allantoin in a combined 0.5%-2.5% w/w of the composition.

In another embodiment, the anti-inflammatory may include a non-steroidal anti-inflammatory drug ("NSAID"). Certain NSAIDs may include acetyl salicylic acid, diclofenac, ibuprofen, ketoprofen, naproxen or piroxicam. NSAIDs are typically found in creams for relief of pain in the treatment of arthritis or hemorrhoids. When applied topically to the skin, NSAIDs help heal and soothe damaged skin with anti-inflammatory properties that work by inhibiting the body's synthesis of prostaglandins which are the messenger molecules in the process of inflammation. Preferably, the composition includes 1.0%-6.0% w/w of diclofenac or ibuprofen.

The moisturizing agents may include jojoba seed oil, almond oil, palm oil, coconut oil, olive oil or castor oil. The moisturizing agent is used to treat dryness associated with skin damage. Preferably, the composition includes 0.5%-10.0% w/w of jojoba seed oil, and specifically 1.0% w/w of jojoba seed oil. jojoba seed oil provides the skin with all day moisturization because its chemical structure is most similar to the human skin oil, sebum. This similarity in structure facilitates skin absorption as well as balance oil production.

The humectant may include hexylene glycol, propylene glycol, butylene glycol, sorbitol or glycerin. Humectants help preserve moisture or water content in the skin and enhances the moisturizing capabilities of the pain relieving composition disclosed herein. Preferably, the composition includes 0.5%-10.0% w/w of hexylene glycol which is hydrophilic meaning it attracts water and prevents the loss of moisture from the skin. Even more preferably, the composition includes 1.0% w/w of hexylene glycol. Alternatively, the composition includes 0.5%-10.0% w/w of glycerin, and more specifically 1.0% w/w of glycerin.

The penetration enhancing agent includes dimethyl sulfoxide (DMSO), ethanol, disodium ethylenediaminetetraacetic (EDTA) or lauramide DEA. The penetration enhancing agent facilitates the absorption of the anesthetic into the cutis to numb the nerves. Preferably, the composition includes 0.5%-5.0% w/w of DMSO, and specifically 2.5% w/w of DMSO. Before hair removal or other painful inflictions to the skin, the DMSO enhances penetration of the anesthetic into the cutis by disordering or 'fluidizing' the lipid structure of the stratum corneum, the outer most layer of the epidermis. DMSO is also known to extract lipids thereby forming aqueous channels within the stratum corneum that increase permeability. This allows the anesthetic to be absorbed through the epidermis and into the dermis to block nerve transmissions, thereby reducing pain during hair removal other painful inflictions to the skin.

The carrier solvent may include water or mineral oil. For example, the carrier solvent includes 52.0%-94.0% w/w of water to add moisture to the skin, increases spreadability properties and provide the composition with a non-greasy feel. In a particularly preferred embodiment, the carrier solvent is deionized water.

Any combination of the above described ingredients could be used to make the pain relieving composition. In an alternative embodiment, the composition may also include a thickener in the range of 2.0%-10.0% w/w of the composition. The thickener may include cetyl alcohol, xanthan gum, behenyl alcohol, carbomer or hydroxypropyl methycellulose. The amount of the thickener agent depends on the desired viscosity, which determines the spreadability, texture and general "feel" the user experiences when the composition is applied and absorbed into the skin. Preferably, the composition includes 3.0%-8.0% w/w of cetyl alcohol to provide the composition with higher viscosity. More specifically, the composition preferably includes 6.5% w/w of cetyl alcohol to give the composition desired viscosity, texture and spreadability.

In yet another embodiment, the composition may further include sodium polyacrylate and caprylyl glycol. Preferably, the composition includes 0.5%-5.0% w/w of sodium polyacrylate to provide skin conditioning properties and 0.05%-4.0% w/w of caprylyl glycol to further stabilize the composition. Even more preferably, the composition includes 1.5% w/w of sodium polyacrylate and 0.3% w/w of caprylyl glycol. Sodium polyacrylate and caprylyl glycol are both emollients which help further soften and moisturize the skin by reducing water loss from the epidermis and helps stabilize the composition. Sodium polyacrylate is known as a waterlock polymer capable of absorbing as much as 400-500 times its mass in water and caprylyl glycol further stabilizes the composition, while providing moisture and skin conditioning properties.

The composition disclosed herein may further include an emulsifier in the range of 0.5%-5.0% w/w. Preferably, the emulsifier includes stearic acid, glyceryl monostearate, polysorbate 60, or potassium cetyl phosphate. Typically, the amount of emulsifier depends on the amount effective to homogenize the composition. In one preferred embodiment, the composition includes 2.5% of stearic acid which provides proper emulsification for the composition. In another embodiment, the composition may include 1.0%-4.5% of polysorbate 60, potassium cetyl phosphate, or a combination of both. For example, polysorbate 60 can be used as an emulsifier to solubilize essential oils into water-based products or lotions and potassium cetyl phosphate functions as a surfactant and emulsifying agent used as a cleansing agent (like a detergent).

In another embodiment, the composition may also include a preservative in the range of 0.0005%-1.0%. The preservative may include potassium sorbate, phenoxyethanol, methylparaben, polyparaben, ethylhexylglycerin, sodium hydroxide, BHT, or tetrasodium EDTA. Preferably, the preservative includes potassium sorbate in the range of 0.0005%-1.0% w/w of the composition and phenoxyethanol in the range of 0.0005%-1.0% w/w. Alternatively, the composition may include 0.001% w/w potassium sorbate and 0.5% w/w phenoxyethanol which would adequately inhibit microorganism development and enhance the composition's shelf-life. In another preferred embodiment, the composition includes at least one of ethylhexylglycerin, sodium hydroxide, BHT, or tetrasodium EDTA in the range of 0.0005%-1.0% w/w. In fact, the composition may include various combinations of multiple preservatives, but it is preferred that the aggregate w/w of all preservatives in the composition do not exceed 1.0% w/w of the composition. In particular, ethylhexylglycerin provides skin conditioning and sodium hydroxide acts as a cleaning agent to dissolve protein-based skin deposits.

In an additional embodiment, the composition may also include an ultraviolet absorber in the range of 0.05%-2.0% w/w of the composition and a colorant in the range of 0.05%-2.0% w/w. The ultraviolet absorber may include benzophenone-4 or benzophenone-3 and the colorant may include any desired color of dye safe for use upon the skin. For example, the colorant may include white, yellow, blue (e.g., blue 1, blue 2, blue 10 or blue 40), green, red, orange or violet. Preferably the dye chosen would not color the skin after the cream is applied. The ultraviolet absorber may include 0.15% of benzophenone-4 to add sunscreen properties to the composition and the colorant may include 0.08% of blue 1 to give the composition a distinct color.

In yet another embodiment, the pain relieving composition may include an emollient in the range of 1.00%-15.00% w/w of the composition. Specific emollients may include C12-15 alkyl benzoate, cetearyl alcohol, isopropyl palmitate, cyclopentasiloxane, cucumis sativus (cucumber) fruit extract, or glycol distearate. In particular, C12-15 alkyl benzoate has other purposes, in addition to being an emollient, such as reducing the greasiness of other oils in the composition, functioning as an anti-tackiness agent, lubricant, binder and wetting agent for mineral-based ingredients. It also works as a solvent, which makes it easier to incorporate ingredients into a day-use moisturizer. C12-15 alkyl benzoate also increases spreadability by having a high surface tension and low viscosity, solubilizes other oils and silicones, and offers occlusion without heaviness (e.g., it is good at getting occlusive powers of shea butter in a lighter feeling lotion). The mixture of fatty alcohols in cetearyl alcohol allows it to act as an emollient, opacifying agent and foam boosting surfactant, including as a non-aqueous viscosity-increasing agent. In this respect, cetearly alcohol confers moisture to the skin and can also be used for purposes of emulsification. Moreover, isopropyl palmitate is a palm oil based product that further acts as a moisturizer, thickening agent, and anti-static; and cyclopentasiloxane is an ingredient commonly used in silicone-based lubricants. It is preferred that the composition include approximately 1.0-2.0% w/w of C12-15 alkyl benzoate, 1.0-2.0% w/w of cetearyl alcohol, 1.0-2.0% w/w of isopropyl palmitate, 1.0-2.0% w/w of cyclopentasiloxane, 1.0-2.0% w/w of cucumis sativus (cucumber) fruit extract, and 1.0-2.0% w/w of glycol distearate. Although, each of the aforementioned emollients can be mixed and matched according to the desired properties of the composition.

Lastly, the composition may further include between 1.0-15.0% of butyrospermum parkii (shea butter), dimethicone, a silicone oil to provide skin protection, ethoxydiglycol (an alcohol used as a drying agent), or sodium hyaluronate, a tissue lubricant.

Although several embodiments have been described in detail for purposes of illustration, various modifications may be made without departing from the scope and spirit of the invention. Accordingly, the invention is not to be limited, except as by the appended claims.

What is claimed is:

1. A pain relieving composition, consisting essentially of:
   a therapeutically effective amount of a numbing agent selected from the group consisting of lidocaine, prilocalne, benzocaine, and tetracaine;
   a therapeutically effective amount of a moisturizing agent selected from the group consisting of jojoba seed oil, palm oil, coconut oil and olive oil;
   a therapeutically effective amount of a penetration enhancing agent selected from the group consisting of dimethyl sulfoxide and disodium ethylenediaminetetraacetic (EDTA);
   a therapeutically effective amount of a humectant selected from the group consisting of sorbitol, glycerine and hexylene glycol;
   a therapeutically effective amount of an emollient selected from the group consisting of sodium polyacrylate and caprylyl glycol; and
   water.

* * * * *